United States Patent [19]
Dean

[11] Patent Number: 5,827,705
[45] Date of Patent: Oct. 27, 1998

[54] MOLECULE AND METHOD FOR IMPORTING DNA INTO A NUCLEUS

[75] Inventor: David A. Dean, Mobile, Ala.

[73] Assignee: South Alabama Medical Science Foundation, Mobile, Ala.

[21] Appl. No.: 822,982

[22] Filed: Mar. 21, 1997

Related U.S. Application Data

[60] Provisional application No. 60/013,863 Mar. 22, 1996 and provisional application No. 60/032,468 Dec. 6, 1996.

[51] Int. Cl.$^6$ .............................. C12N 5/10; C12N 15/86; C12N 15/88; C07H 21/04
[52] U.S. Cl. ..................................... 435/172.3; 435/320.1; 435/325; 435/348; 435/252.3; 435/254.2; 435/419; 536/23.1; 536/24.1
[58] Field of Search ................... 435/69.1, 172.1, 435/172.3, 320.1, 5, 6, 325, 348, 352, 363, 366, 410, 419, 254.1, 254.11, 252.3, 254.2; 536/23.1, 23.72, 24.1; 424/93.2, 93.6; 514/44

[56] References Cited

PUBLICATIONS

Ishii, N., et al., J Virol 68 (12) :8209–8216 (Dec. 1994).
Feldherr, C., et al., Exp Cell Res 213 (1) :164–171 (Jul. 1994).
Dean, D.A., and Kasamatsu, H., J Biol Chem 269(7) :4910–4916 (Feb. 18, 1994).
Xue, Z., et al., Eur J Cell Biol 62(1) :13–21 (Oct. 1993).
Feldherr, C.M., et al., Proc Natl Acad Sci USA 89 (22) :11002–11005 (Nov. 15, 1992).
Yoneda, Y., et al., Exp Cell Res 201(2) :313–320 (Aug. 1992).
Lassner, M.W., et al., Plant Mol Biol 17(2) :229–234 (Aug. 1991).
Rihs, H.P. , et al., EMBO J 10(3) :633–639 (Mar. 1991).
Clever, J., and Kasamatsu, H., Virology 181(1) :78–90 (Mar. 1991).
Ono, T., e al., Neurosci Lett 117(3) :259–263 (Sep. 18, 1990).
Gharakhanian, E., and Kasamatsu, H., Virology 178(1) :62–71 (Sep. 1990).
Lobl, T.J., et al., Biopolymers 29(1): 197–203 (Jan. 1990).
Wychowski, C., et al., EMBO J 5(10) :2569–2576 (Oct. 1986).
Graessmann, M., et al., Nucl Acids Res 17(16) :6603–6612 (1989).
Dean, D.A., Abstract #313 of the Keystone Symposia on Molecular and Cellular Biology, Taos, New Mexico, Feb. 4–10, 1996.

*Primary Examiner*—David Guzo
*Attorney, Agent, or Firm*—Jaeckle Fleischmann & Mugel, LLP; Susan J. Braman, Esq.

[57] ABSTRACT

The invention provides a nuclear targeting molecule having a nucleic acid sequence which consists of SEQ ID NO:1 or a nuclear targeting portion of SEQ ID NO:1. The invention further provides a plasmid for targeting a DNA molecule into the nucleus of a host cell. The plasmid comprises the nuclear targeting molecule (having SEQ ID NO:1 or a nuclear targeting portion of SEQ ID NO:1) and a DNA molecule to be targeted to a nucleus. This plasmid of the subject invention can be introduced into various host cells, and the nuclear targeting molecule will target the DNA molecule to the nucleus of the host cell. Thus, the invention further provides a method of targeting a DNA molecule into the nucleus of a host cell. The method comprises providing a plasmid (the plasmid comprising the nuclear targeting molecule and the DNA molecule to be targeted) and introducing the plasmid into the cytoplasm of the host cell. In this method, the nuclear targeting molecule targets the DNA molecule into the nucleus of the host cell.

32 Claims, 8 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 372 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
AAGCTTTTTG  CAAAAGCCTA  GGCCTCCAAA  AAAGCCTCCT  CACTACTTCT  GGAATAGCTC      60

AGAGGCCGAG  GCGGCCTCGG  CCTCTGCATA  AATAAAAAAA  ATTAGTCAGC  CATGGGGCGG     120

AGAATGGGCG  GAACTGGGCG  GAGTTAGGGG  CGGGATGGGC  GGAGTTAGGG  GCGGGACTAT     180

GGTTGCTGAC  TAATTGAGAT  GCATGCTTTG  CATACTTCTG  CCTGCTGGGG  AGCCTGGGGA     240

CTTTCCACAC  CTGGTTGCTG  ACTAATTGAG  ATGCATGCTT  TGCATACTTC  TGCCTGCTGG     300
```

```
GGAGCCTGGG  GACTTTCCAC  ACCCTAACTG  ACACACATTC  CACAGCTGGT  TCTTTCCGCC      360

TCAGAAGGTA  CC                                                              372
```

MOLECULE AND METHOD FOR IMPORTING DNA INTO A NUCLEUS

This application claims priority of U.S. Provisional Patent application No. 60/013,863, filed Mar. 22, 1996, and of U.S. Provisional Patent application No. 60/032,468, filed Dec. 6, 1996.

FIELD OF INVENTION

The subject invention is directed to a molecule and method for importing DNA into the nucleus of a cell, and more particularly to a nuclear targeting molecule which can be used to target a DNA molecule to the nucleus of a host cell.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Intracellular macromolecular transport into and out of the nucleus occurs through the nuclear pore complex (NPC) (for recent reviews see Hicks and Raikhel, 1995; Melchoir and Gerace, 1995). Microinjection and digitonin-permeabilized cell experiments have led to a model for protein nuclear import in which a nuclear transport signal (NTS)-containing protein is bound by a cytoplasmic heterodimeric protein complex, termed either karyopherin α/β or importin α/β (Adam and Adam, 1994; Görlich et al., 1994; Moroianu et al., 1995; Radu et al., 1995; Weis et al., 1995). This complex then docks at the NPC where the GTPase Ran and NTF2 facilitate the translocation of the NTS-protein complex into the nucleus (Melchoir et al., 1993; Moore and Blobel, 1993; Moore and Blobel, 1994). This model fully supports the previous findings that protein nuclear import is a two step process: the energy-independent binding of substrate to the NPC, and the energy-requiring translocation reaction (Newmeyer and Forbes, 1988; Richardson et al., 1988).

It has recently been shown that certain ribonucleic acids (RNAs) including several of the U small nuclear ribonucleoproteins (snRNPs) appear to use the same pathway for their import into the nucleus (Hamm et al., 1990; Michaud and Goldfarb, 1991; Michaud and Goldfarb, 1992; O'Neill et al., 1995). This type of pathway has been proposed to occur in the nuclear import of Influenza A RNAs. Using permeabilized cells, it was shown that the viral RNAs could be imported only in the presence of both the karyopherin α/β and RAN/p10 complexes, which are required for protein nuclear import, and the viral nucleocapsid proteins, which bind to the viral RNA and contain an NTS (O'Neill et al., 1995). However, other pathways which may share common proteins and factors do exist (Michaud and Goldfarb, 1992; Dean and Kasamatsu, 1994; Cserpan and Udvardy, 1995).

In contrast to what is known about protein and snRNP nuclear entry, the mechanism of entry of exogenous deoxyribonucleic acid (DNA) into the nucleus is largely unknown. All studies involving recombinant eukaryotic gene expression rely on the ability of the introduced gene to become nuclear to function, regardless of how the DNA is introduced into the cell. Nuclear localization of extrachromosomal DNA is also important in a number of viral life cycles (Fields et al., 1990). While the nuclear import of exogenous DNA has been addressed in several experimental systems, including that of the single stranded Ti-DNA from *Agrobacterium tumefaciens* in tobacco (Escudero et al., 1995; Zupan and Zambryski, 1995) and of the human immunodeficiency virus (HIV) pre-integration complex (PIC) in quiescent T cells (Bukrinsky et al., 1992; Bukrinsky et al., 1993; von Schwedler et al., 1994), no general mechanisms have been elucidated. The nuclear import of HIV PICs appears to depend on the presence of a functional NTS within the matrix protein which is present in the PIC (Bukrinsky et al., 1992; Bukrinsky et al., 1993; von Schwedler et al., 1994).

It has recently been shown that plasmid DNA injected into multinucleated rat myotubes becomes nuclear within 10 to 20 hours as assayed by β-galactosidase activity expressed from the lacZ gene encoded in the injected plasmids (Dowty et al., 1995). This expression was inhibited by wheat germ agglutinin (WGA), suggesting import through the NPC (Finlay et al., 1987). However, when the DNA was labeled with biotin and injected into the cells, no nuclear DNA was detected. Similarly, only small numbers of colloidal gold particles, representing gold-labeled DNA, could be detected in the nuclei of a few of the injected cells. Additionally, gene expression was unaffected by energy depletion, further complicating the role of the NPC and the nuclear "import".

An intrinsic problem to many of these experiments is that gene expression is a measure not only of DNA nuclear localization, but also of transcription factor nuclear import, transcription, messenger RNA (mRNA) processing and export, and translation. Thus, the effects of agents that alter any of these processes could be misinterpreted as directly modulating DNA import.

The success of many proposed gene therapy techniques will likely rely on the ability to import exogenous DNA into the nucleus of a host cell. A need exists, therefore, for the elucidation of a mechanism for successfully importing such exogenous DNA.

SUMMARY OF THE INVENTION

This need is met by the nuclear targeting molecule and method of the subject invention. More particularly, the invention provides a nuclear targeting molecule having a nucleic acid sequence which consists of SEQ ID NO:1 or a nuclear targeting portion of SEQ ID NO:1. The invention further provides a plasmid for targeting a DNA molecule into the nucleus of a host cell. The plasmid comprises the nuclear targeting molecule and a DNA molecule to be targeted to a nucleus. This plasmid of the subject invention can be introduced into various host cells, and the nuclear targeting molecule will target the DNA molecule to the nucleus of the host cell.

Thus, the invention further provides a method of targeting a DNA molecule into the nucleus of a host cell. The method comprises providing a plasmid (the plasmid comprising the nuclear targeting molecule and the DNA molecule to be targeted) and introducing the plasmid into the cytoplasm of the host cell. In this method, the nuclear targeting molecule targets the DNA molecule into the nucleus of the host cell.

BRIEF DESCRIPTION OF THE FIGURES

These and other features and advantages of this invention will be evident from the following detailed description of preferred embodiments when read in conjunction with the accompanying drawings in which.

DETAILED DESCRIPTION OF THE INVENTION

Figure 1:
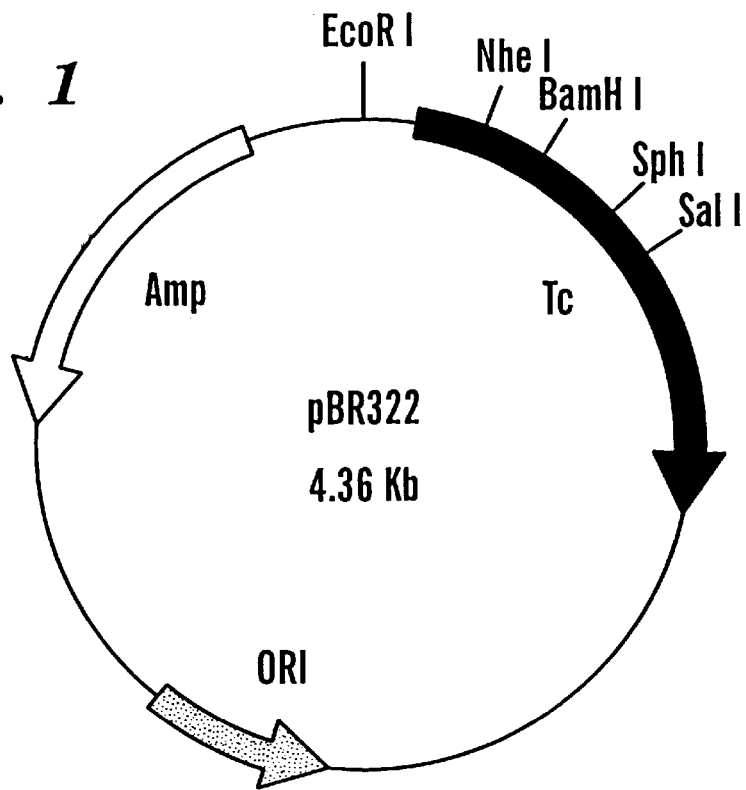
FIG. 1 is a map of the plasmid pBR322.

Nuclear import of plasmid DNA in non-dividing cells is a process essential to the success of numerous viral life cycles, gene therapy protocols, and gene expression experiments. According to the subject invention, intact protein-free simian virus 40 (SV40) DNA was cytoplasmically-injected into cells and its subcellular localization was followed directly by fluorescence in situ hybridization. An advantage of this detection approach is that it does not rely on the transcriptional activity or post-transcriptional processes that must occur in order to detect the expression of a gene product as an indicator of DNA nuclear import.

SV40 DNA localized to the nucleus consistent with a mechanism of transport through the nuclear pore complex (NPC). Import was inhibited by the addition of the NPC-inhibitory agents, wheat germ agglutinin (WGA) and an anti-nucleoporin antibody mAb414, as well as by energy depletion. Transport of the DNA also appeared to be a multistep process with the DNA accumulating at the nuclear periphery before its import. Nuclear import was sequence-specific. RNA polymerase II promoters and the SV40 origin of replication supported import, whereas bacterial sequences alone and other SV40-derived sequences did not. The majority of the imported DNA co-localized with the SC-35 splicing complex antigen, suggesting that the intranuclear DNA localizes to areas of transcription or message processing. This link to transcription was strengthened by the finding that inhibition of transcription blocked DNA import. Taken together, these results support a model in which plasmid DNA nuclear import is coupled to active transcription.

The inhibition of plasmid DNA nuclear localization by WGA, mAb414, and energy-depletion, all of which also inhibit NTS-dependent, NPC-mediated protein nuclear import, suggests that exogenous DNA uses a similar pathway as do NTS-containing proteins and certain RNPs (Davis and Blobel, 1986; Finlay et al., 1987; Newmeyer and Forbes, 1988; Richardson et al., 1988; Michaud and Goldfarb, 1992; O'Neill et al., 1995).

The subject invention thus provides a nuclear targeting molecule having a nucleic acid sequence which consists of SEQ ID NO:1 or a nuclear targeting portion of SEQ ID NO:1. Preferably, the nuclear targeting portion of SEQ ID NO:1 is selected from the group consisting of nucleotides 1 to 233 of SEQ ID NO:1, 1 to 115 of SEQ ID NO:1, 110 to 372 of SEQ ID NO:1, 110 to 233 of SEQ ID NO:1, 201 to 278 of SEQ ID NO:1, and 273 to 372 of SEQ ID NO:1. As will be readily understood by those skilled in the art, numerous nucleotides in SEQ ID NO:1 or a nuclear targeting portion of SEQ ID NO:1 are likely to be filler or spacer nucleotides which are not critical to function. An A or G which is such a filler or spacer nucleotide could thus readily be interchanged with a C or T, for example, without affecting the function of the molecule. Such nucleotides could also readily be deleted. SEQ ID NO:1, as shown herein, is a portion of the SV40 genome which generally includes the enhancer and promoter regions of SV40. Additional nucleotides 5' or 3' to SEQ ID NO:1 in the SV40 genome could also be added to SEQ ID NO:1 without detracting from the molecule's nuclear targeting function. Such additions, deletions, and substitutions could be made by methods known in the art, including site directed mutagenesis.

The nuclear targeting molecule from SV40 is a DNA molecule, and can be isolated from SV40 or synthetically constructed based on the desired nucleotide sequence. As used herein, the term "isolated" when used in conjunction with SV40 refers to a nucleic acid sequence separated from the entire SV40 genome or from another vector which includes the desired portion of the SV40 genome.

Figure 4:
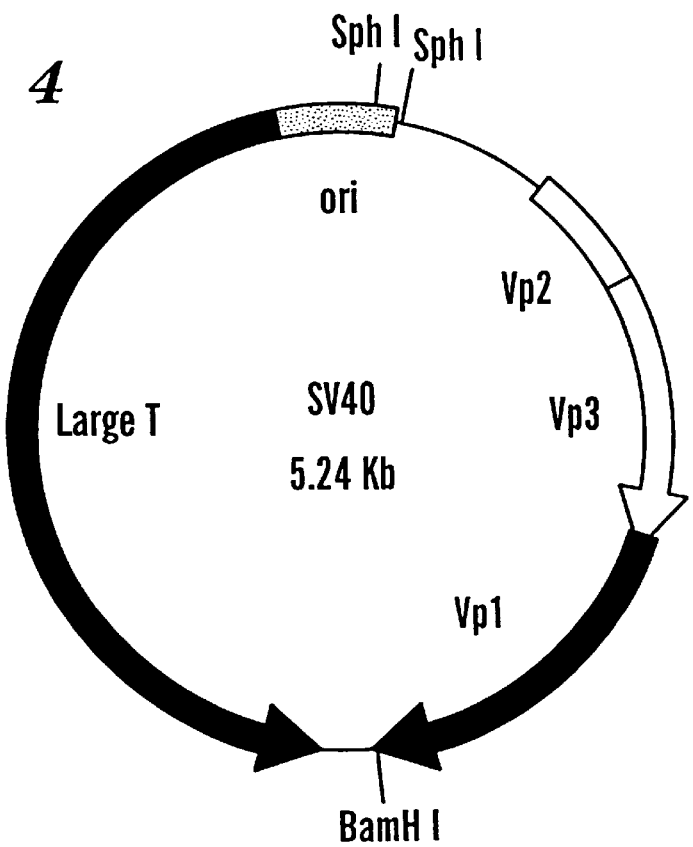
FIG. 4 is a map of SV40.
Figure 9:
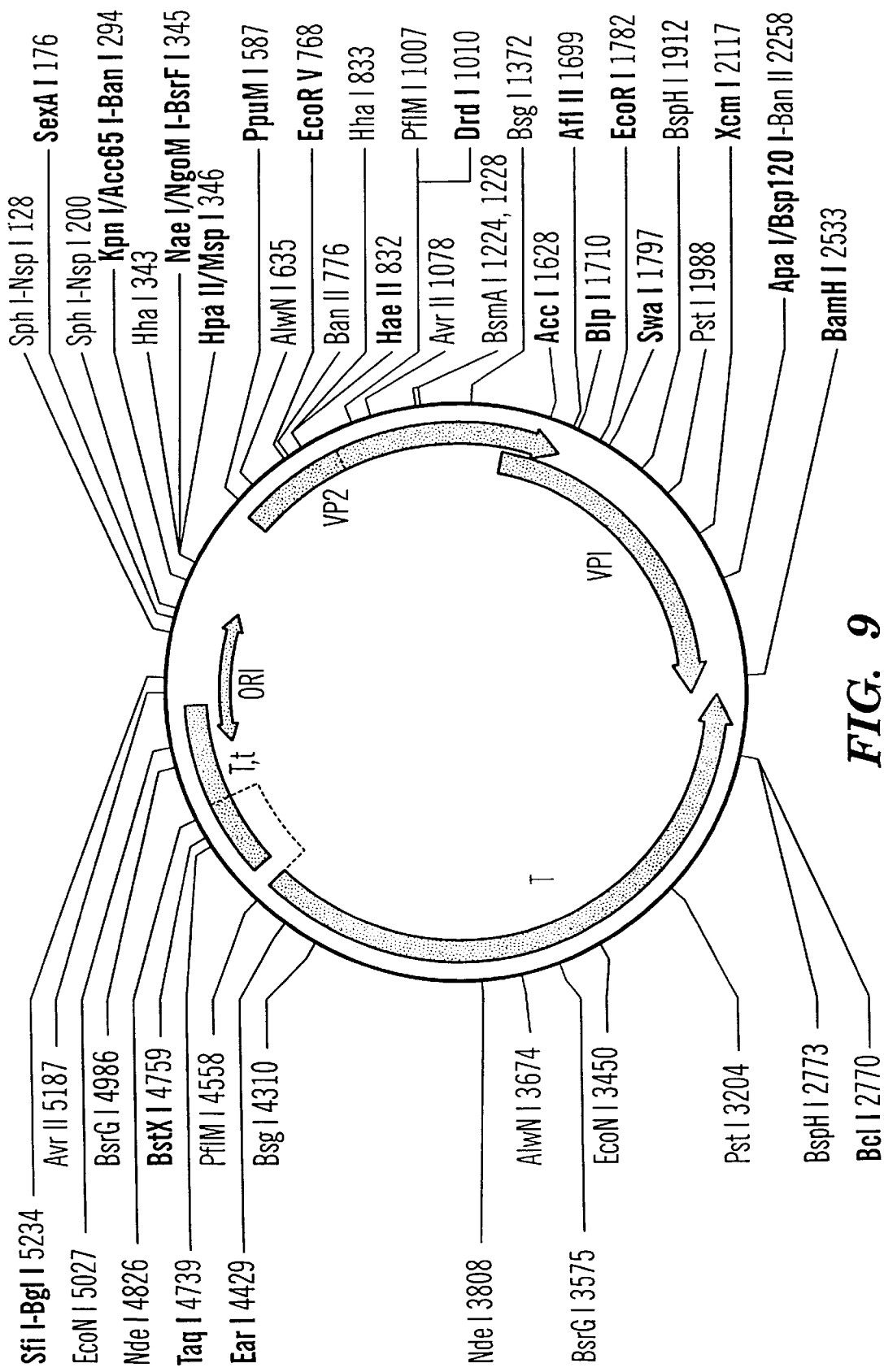
FIG. 9 is a map of SV40 showing the restriction sites for those enzymes which cut the molecule once or twice; the unique sites are shown in bold type.

SV40 is a small, icosahedral, papovavirus. The DNA is a double-stranded circle 5,243 base pairs in length. Numbering of the sequence of SV40 begins within the unique BglI site at the origin of replication. Numbering proceeds clockwise around the molecule in the direction of late genes to early genes. FIG. 4 is a map of SV40, and FIG. 9 is a map of SV40 showing the restriction sites for those enzymes which cut the SV40 molecule once or twice. The entire sequence of the SV40 genome has been published by Reddy et al. 1978 and Fiers et al. 1978. The contents of each of these references is hereby incorporated by reference to more fully describe the state of the art to which the subject invention pertains. SEQ ID NO:1 is the portion of the entire SV40 genome from the HindIII site at nucleotide 5171 to the KpnI site at nucleotide 294. Thus, SEQ ID NO:1 represents nucleotides 5171–5243 and 1–299 of the entire SV40 circular genome.

The nuclear targeting molecule is most readily used by providing a plasmid (an extrachromosomal piece of DNA) for targeting a DNA molecule into a nucleus of a host cell. The plasmid, in its most basic form, comprises a nuclear targeting molecule having a nucleic acid sequence which consists of SEQ ID NO:1 or a nuclear targeting portion of SEQ ID NO:1 (see above for preferred nuclear targeting portions), and a DNA molecule to be targeted to a nucleus of a host cell. The structural connection of the two parts of the plasmid are that the two are contained on the same plasmid. Since the DNA molecule to be targeted need not be under expressional control of the nuclear targeting molecule (see below), the DNA molecule does not need to be "downstream" of the nuclear targeting molecule. As should be readily understood by those skilled in the art, "upstream" and "downstream" refer to location in the plasmid relative to the orientation of a gene (the DNA molecule to be targeted). For example, if a gene is presented in a 5' to 3' orientation, sequences to the 5' region of the gene are "upstream" and sequences to the 3' region of the gene are "downstream". In the case of a circular DNA molecule, upstream and downstream are given meaning in relation to a given gene (i.e., see FIG. 4 where the circular genome of SV40 is illustrated; note the opposite orientation of the large T gene from the VP2, VP3, or VP1 genes; downstream of VP1 is also downstream from large T).

The DNA molecule to be targeted to the nucleus generally encodes a protein or enzyme which would be desirable to express in the nucleus of a cell, and generally is exogenous DNA (i.e., such an encoded protein or enzyme is not being expressed in the host cell or is being expressed at very low levels). Many examples of DNA molecules for which it would be desirable to import the molecules into a host cell should be readily apparent to those skilled in the art. For example, many proposed gene therapy techniques would benefit from the ability to import a DNA molecule into the nucleus according to the subject invention. In just the last twelve months, numerous examples of DNA molecules which could be imported according to the subject invention has been published. The following are examples, for illustration only, of suitable DNA molecules. Vrionis et al. 1995 disclose that the expression of herpes simplex virus thymidine kinase (HSV-tk) in a host cell may be useful in the treatment and/or prevention of brain tumors. Knowles et al. 1995 disclose that the expression of the cystic fibrosis transmembrane conductance regulator in pulmonary epithelia may be useful in the treatment and/or prevention of cystic fibrosis lung disease. Rowland et al. 1995 disclose that the expression of missing or defective proteins may be useful in the treatment and/or prevention of cardiovascular disease. Baru et al. 1995 disclose that the expression of clotting factor IX may be useful in the treatment and/or prevention of hemophilia B. Brownlee 1995 disclose that the expression of clotting factor VIII may be useful in the treatment and/or prevention of hemophilia A. Osborne et al. 1995 disclose that the expression of erythropoietin may be useful in the treatment of anemia associated with chronic renal failure, cancer, and HIV infections. Kojima et al. 1995 disclose that the expression of brain-derived neurotrophic factor may be useful in the treatment and/or prevention of neurodegenerative diseases. Betz et al. 1995 disclose that the expression of interleukin-1 receptor antagonist protein (IL-1ra) may be useful in the reduction of ischemic brain injury damage. Vaulont et al. 1995 disclose that the expression of adenosine deaminase may be useful in the treatment and/or prevention of an autosomal recessive form of severe combined immunodeficiency (SCID). Ekhterae and Stanley 1995 disclose that the expression of tissue plasminogen activator (tPA) may be useful in the enhancement of fibrinolytic activity of vascular cells. Stevenson et al. 1995 disclose that the expression of apolipoprotein E (apo E) may be useful in the treatment and/or prevention of hyperlipidemias. Phaneuf et al. 1995 disclose that the expression of fumarylacetoacetate hydrolase (FAH) may be useful in the treatment and/or prevention of type 1 hereditary tyrosinemia. Each of the above references provides a separate example of the applicability of the subject invention to nuclear importation of many different DNA molecules, for many different reasons. As should be readily apparent from the above examples, many applications of the method of the subject invention could be in the area of gene therapy, where a protein or enzyme of interest can be imported into the nucleus of the desired host cell.

The DNA molecule to be targeted could also express an RNA that does not code for a protein. Examples would be an "antisense oligonucleotide" that could inhibit the translation or stability of a cellular mRNA, or a stable RNA such as a tRNA, a rRNA, a UsnRNA (involved in mRNA splicing), or 7SL RNA which is part of the signal recognition particle (SRP) for protein translocation into the endoplasmic reticulum. Antisense RNAs are very popular for their potential to alter cellular mRNA levels for desired genes (Scanlon et al. 1995). Another example would be "ribozymes", RNAs that repair mutant mRNAs (Sullenger and Cech 1994).

The plasmid of the subject invention may contain other elements in addition to the nuclear targeting molecule and the DNA molecule to be targeted. For example, it may be desirable to include a bacterial origin of replication (such as ori C for replication in *Escherichia coli*, or the origin of replication of *Bacillus subtilis* for replication therein, or the origin of replication of *Pseudomonas aeruginosa* for replication therein, etc.) so that the plasmid can be maintained and replicated in a bacterial host. Such an embodiment of the plasmid of the subject invention could also include a selection marker for selecting bacterial colonies which contain the subject plasmid. Such selection or biological markers are well known in the art. In bacteria, these are commonly drug-resistance genes. Drug or antibiotic resistance is used to select bacteria that have taken up cloned DNA from the much larger population of bacteria that have not.

A selection marker can also be included in the plasmid to identify mammalian cells which have taken up the plasmid DNA. In the early mammalian gene transfer experiments involving viral genes, the transfer of exogenous DNA into cells was detected because the DNA had a biological activity; it led to production of infectious virus or produced stable changes in the growth properties of the transfected cells. The herpes simplex virus thymidine kinase (HSV tk) gene can be used as a selectable genetic marker in mammalian cells in much the same way that drug-resistance genes work in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including:

aminoglycoside phosphotransferase (APH), using the drug G418 for selection which inhibits protein synthesis; the APH inactivates G418;

dihydrofolate reductase (DHFR):Mtx-resistant variant, using the drug methotrexate (Mtx) for selection which inhibits DHFR; the variant DHFR is resistant to Mtx;

hygromycin-B-phosphotransferase (HPH), using the drug hygromycin-B which inhibits protein synthesis; the HPH inactivates hygromycin B;

thymidine kinase (TK), using the drug aminopterin which inhibits de novo purine and thymidylate synthesis; the TK synthesizes thymidylate;

xanthine-guanine phosphoribosyltransferase (XGPRT), using the drug mycophenolic acid which inhibits de novo GMP synthesis; XGPRT synthesizes GMP from xanthine;

adenosine deaminase (ADA), using the drug 9-β-D-xylofuranosyl adenine (Xyl-A) which damages DNA; the ADA inactivates Xyl-A; and multidrug resistance (MDR), which is also known as the P-glycoprotein (Licht et al. 1995).

Gene amplification can also be used to obtain very high levels of expression of transfected gene. When cell cultures are treated with Mtx, an inhibitor of a critical metabolic enzyme, DHFR, most cells die, but eventually some Mtx-resistant cells grow up. A gene to be expressed in cells is cotransfected with a cloned dhfr gene, and the transfected cells are subjected to selection with a low concentration of Mtx. Resistant cells that have taken up the dhfr gene (and, in most cases, the cotransfected gene) multiply. Increasing the concentration of Mtx in the growth medium in small steps generates populations of cells that have progressively amplified the dhfr gene, together with linked DNA. Although this process takes several months, the resulting cell cultures capable of growing in the highest Mtx concentrations will have stably amplified the DNA encompassing the dhfr gene a hundredfold or more, leading to significant elevation of the expression of the cotransfected gene.

It may also be desirable to include, as an element of the plasmid according to the subject invention, a molecule encoding a promoter to control expression of the DNA molecule to be targeted. Such a promoter sequence would need to be positioned upstream from the DNA molecule to effectively control expression of the DNA molecule. RNA polymerase normally binds to the promoter and initiates transcription of a gene (the DNA molecule) or a group of linked genes and regulatory elements (operon). Promoters vary in their strength, i.e., ability to promote transcription. For the purpose of expressing the DNA molecule of the invention, it is desirable to use strong promoters in order to obtain a high level of transcription and, hence, expression of the gene. The promoter could also be a tissue-specific promoter which only turns on in the correct tissue, or a developmentally regulated promoter which only turns on at a certain time in the development of a cell or tissue. Examples include the alpha-actin promoter which is expressed in muscle cells (Shimizu et al. 1995), the beta globin promoter which is expressed in adult erythrocyte progenitor cells, or the gamma globin promoter which is expressed in fetal erythrocyte progenitor cells (Stamatoyannopoulos and Nienhuis 1994). Depending upon the host cell system utilized, any one of a number of suitable promoters can be used. In bacterial host cells, suitable promoters include, for example, the lac promoter, trp promoter, recA promoter, ribosomal RNA promoter, the $P_R$ and $P_L$ promoters of coliphage lambda, and others, including but not limited to, lacUV5, ompF, bla, lpp and the like, and the nos promoter. Additionally, a hybrid trp-lacUV5 (tac) promoter or other $E.$ $coli$ promoters produced by recombinant DNA or other synthetic DNA techniques can be used to provide for transcription of the DNA molecule of the invention. Other promoters for use in plant cells include, for example, the small subunit chlorophyll A/B binding polypeptide, the 35S promoter of cauliflower mosaic virus, and promoters isolated from plant genes, including the Pto promoter itself (Vallejos et al. 1986) to direct high levels of transcription of adjacent DNA segments. Suitable promoters for expression of genes in animal cells include, for example, the beta-actin promoter, cytomegalovirus (CMV) promoter, Adenovirus major late promoter, SV40 early promoter, SV40 late promoter, Thymidylate kinase (TK) promoter, and the Rous Sarcoma Virus (RSV) LTR-promoter. An example of a suitable promoter for use in insect cells is the AcMNPV polyhedrin promoter.

Bacterial host cell strains and expression vectors can be chosen which inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promoter of lambda can be induced by an increase in temperature in host cells containing a temperature sensitive lambda repressor, e.g., c1857. In this way, greater than 95% of the promoter-directed transcription may be inhibited in uninduced cells. Thus, expression of the DNA molecule of the invention can be controlled.

When cloning in a eucaryotic host cell, enhancer sequences (e.g., the 72 bp tandem repeat of SV40 DNA or the retroviral long terminal repeats of LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have the remarkable ability to function upstream from, within, or downstream from eucaryotic genes. Therefore, the position of the enhancer sequence with respect to the inserted gene is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in $E.$ $coli$ requires a Shine-Dalgarno (SD) sequence about 7–9 bases 5' to the initiation codon (ATG) to provide a ribosomal binding site. Thus, any SD-ATG combination that can be utilized by host cell ribosomes can be employed. Such combinations include but are not limited to the SD-ATG combination from the CRO gene or the N gene of coliphage lambda, or from the $E.$ $coli$ tryptophan E, D, C, B or A genes. Additionally, any SD-ATG combination produced by recombinant DNA or other techniques involving incorporation of synthetic nucleotides can be used.

In accordance with the subject invention, the DNA of the plasmid as described herein is targeted into the nucleus of a host cell, where the DNA molecule to be targeted is expressed. Since the nuclear-localized plasmid DNA will eventually be degraded, it may be desirable for long term expression of the DNA molecule in the nucleus of the host cell to integrate the plasmid DNA into the genome of the host cell. In such an embodiment, the plasmid of the subject invention further includes a molecule to direct integration of the DNA molecule into the genome of the host cell. Such integration sequences are known in the art, and include, for example, the inverted terminal repeats of adeno-associated virus (ITRs), retroviral long terminal repeats (LTRs), and other viral sequences shown to cause incorporation or integration of the viral genome into the host cell genome. For integration into plant genomes, the left and right Agrobacterium T-DNA border sequences allow the integration of exogenous DNA located between the left and right T-DNA border sequences into a plant cell.

As should be readily apparent, various additional elements can be included in the plasmid of the subject invention depending upon the desired goal. For ease in constructing various embodiments of the plasmid, the basic plasmid (comprising the nuclear targeting molecule and the DNA molecule to be targeted) can also contain a number of unique restriction enzyme sites for insertion of the additional molecules or elements. As used herein, a "unique" restriction enzyme site refers to the presence of only one cleavage site for a particular restriction endonuclease within the plasmid DNA. That particular restriction endonuclease (or restriction enzyme) will, therefore, only cleave the DNA of the plasmid at that one location or "unique" site. These unique restriction sites can be provided in the plasmid of the subject invention by including a polylinker as an element of the plasmid. As used herein, a "polylinker" refers to a sequence which contains many restriction enzyme recognition sequences that are present only once in the vector or plasmid, i.e., unique restriction sites. The plasmid of the subject invention may also contain restriction sites that occur twice in close proximity (i.e., the flanking sites of the polylinker) and these could also be used to clone in sequence between the sites.

Having constructed the plasmid according to the subject invention, a host cell comprising the plasmid is also provided by the subject invention. As indicated above, for maintenance and propagation of the plasmid, a bacterial host cell (such as *Escherichia coli*) may be used. Bacterial host cells for maintenance and propagation offer the advantages of being easy to work with and capable of rapid reproduction and therefore propagation of the plasmid.

In use however, the DNA molecule to be targeted to the nucleus of a host cell is most likely to express a product useful in animal (including, for example, mammals, birds, amphibians, reptiles and fish), plant, yeast, or insect host cells. Suitable host cells are any cells into which a DNA molecule is desired to be introduced. For example, and referring to the many possible uses of the subject invention discussed above, the host cell may be a pulmonary epithelial cell where gene therapy of cystic fibrosis lung disease is being treated and/or prevented. Vascular cells may be a suitable host cell where tPA is desired to be expressed. Plant cells, such as of various crop plants including potato, tomato, cereals, etc., may be suitable host cells where plant disease resistance genes are desired to be expressed. Yeast cells, such as *Saccharomyces cerevisiae*, may be suitable host cells for applicability of the invention to industrial fermentation processes. In a particular insect cell, it may be desirable to express an insecticide resistance gene in order to select for that insect after exposing an environment to the insecticide. Many other suitable host cells should be readily apparent, as the invention has broad applicability to various host cells and various DNA molecules to be imported into the nucleus thereof. The importation of DNA into the nucleus of a host cell may also be desirable in vitro, using various cells lines known in the art, such as, for example, the mammalian cells identified as NIH3T3 cells, Hela cells, COS cells, and CHO cells, and the insect cell lines identified as Drosophila Schneider, Drosophila $K_c$, and Sf9.

A viral vector may provide the means for introducing the plasmid into the host cell. For example, the plasmid may be introduced into an adenovirus, retrovirus, adeno-associated virus, vaccinia virus, or herpes simplex virus vector and these viral vectors can then infect a mammalian cell in order to get the plasmid DNA into the cytoplasm and/or nucleus of the mammalian cell. Other mammalian viruses could similarly be used. The plasmid could also be introduced into an insect virus, such as baculovirus, for introduction into an insect cell, or a plant virus for introduction into a plant cell.

The nuclear targeting molecule of the subject invention also offers the advantage of being able to target a DNA molecule to the nucleus of a non-dividing host cell. Non-dividing cells include two classes of cells: those that are not dividing (quiescent) and those that cannot divide (i.e., many terminally differentiated cell types). When cells leave mitosis and are finished dividing, they enter the G1 phase of the cell cycle and then come to a halt at G0 (G zero). At this point they are "growth-arrested"; protein synthesis is decreased as is transcription. Upon stimulation, most cells will exit G0 and continue on with the cell cycle, leading to division. However, many cells will remain in this G0 state for a long time. Human liver cells, in the absence of liver damage, will divide only once or twice a year while gut epithelia will divide twice a day. The period of quiescence for each type of cell is different, but if it is greater than a week, the method of the subject invention is especially applicable.

An example of quiescent cells are hematopoeitic stem cells (CD34+ cells). These cells have the potential to divide and self-renew, but they are normally quiescent until stimulated to divide. These cells are a desired target for gene therapy (sickle cell disease, thalasemia, SCID), and the subject method provides a method to get DNA into the cells even though they normally do not divide. Other quiescent cells include fibroblasts in the absence of tissue damage, liver cells in the absence of liver damage, and skeletal muscle cells (these are classic "post-mitotic cells" ). Non-dividing, terminally-differentiated cells are sometimes called "Permanent cells" . Many cells are produced during embryogenesis in numbers that will suffice for the lifetime of the organism. Thus, once they divide and differentiate, they will never divide again. These terminally-differentiated or permanent cells include most neurons and nerve cells; non-dividing differentiated epithelial cells (i.e., top layers of skin that are still living or villus cells of the gut lumen); muscle cells of the heart; auditory hair cells of the ear; and lens cells of the eye.

For a general discussion of non-dividing cells, including quiescent and terminally differentiated cells, see Porth 1994 and Cotran 1994. Additional references describing these types of cells are Seshadri and Campisi 1989 (fibroblasts); Ponchio et al. 1995 and Young et al. 1996 (hematopoietic cells); Langan and Slater 1991 (astroglia); Datta 1995 (neuroblasts); Allen et al. 1995 (skeletal muscle); and Vick et al. 1992 (oligodendrocytes).

Having thus described the nuclear targeting molecule and plasmid according to the subject invention, as well as suitable host cells into which the plasmid can be introduced, the invention further provides a method of targeting a DNA molecule into the nucleus of a host cell. The method comprises first providing a plasmid according to the subject invention, and then introducing the plasmid into the cytoplasm of the host cell (see above for description of the plasmid and the host cell). The nuclear targeting molecule which is an element of the plasmid targets the DNA molecule which is another element of the plasmid to the nucleus of the host cell.

Various methods are known in the art for introducing nucleic acid molecules into host cells. One method is microinjection, in which DNA is injected directly into the cytoplasm of cells through fine glass needles. Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller (1989). Various viral vectors have also been used to transform mammalian cells, such as bacteriophage, vaccinia virus, adenovirus, retrovirus, and adeno-associated virus (AAV) (Berns and Giraud 1995).

As indicated, the method of the subject invention requires the use of a plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in procaryotic and eucaryotic cells. The DNA sequences are cloned into the plasmid vector using standard cloning procedures known in the art, as described by Sambrook et al. (1989).

If the plasmid is to be introduced into plant cells, the methods of introduction may differ slightly. The plasmid can be introduced into *Agrobacterium tumefaciens*. This introduction can be accomplished using methods known to those in the art, including electroporation, or particle bombardment. Another method that can be used to introduce the plasmid into *Agrobacterium tumefaciens* is triparental mating. In a triparental mating, the *Escherichia coli* containing the plasmid, a second *Escherichia coli* containing a helper plasmid, and an Agrobacterium are combined, resulting in introduction of the plasmid DNA into the Agrobacterium. The Agrobacterium cells are then screened using a selection marker for the presence of the plasmid DNA therein. Those cells containing the plasmid DNA are then used for further experiments.

The plasmid can also be introduced into a plant cell. One method for introduction of the plasmid into a plant cell is Agrobacteriumn-mediated transformation of the plant cell (stable or transient). Briefly, the tissue of plants is contacted with an inoculum of the Agrobacterium transformed with the plasmid (with exogenous DNA therein). Generally, this procedure involves inoculating the plant tissue with a suspension of the bacteria and incubating the tissue for 48 to 72 hours on regeneration medium without antibiotics at 25°–280° C.

In practice, the method of Agrobacterium-mediated transformation can involve a three-step process. The plasmid DNA is first analyzed in an *Escherichia coli* host cell, and is then introduced into an *Agrobacterium tumefaciens* host cell, which is then used for Agrobacterium-mediated transfer of the T-DNA within the plasmid to the plant cell. Generally, only a portion of the T-DNA border sequences and DNA located therebetween is transferred into the plant cell by such Agrobacterium-mediated transfer. Therefore, any exogenous DNA for transfer into the plant cell should be located within the plasmid between the T-DNA border sequences.

The leaf disk technique can be utilized in conjunction with Agrobacterium-mediated transformation. Briefly, wounded plant cells (such as leaves, roots and stems) are cultured briefly with Agrobacterium cells to initiate transfer of the T-DNA from the Agrobacterium to the plant cell. After several days, the plant tissue is transferred to shoot-inducing media that contains a selective agent. After shoots are formed, the shoots are transferred to a medium that stimulates root formation.

Another method for introduction of the plasmid into a plant cell is by transformation of the plant cell cytoplasm, such as by particle bombardment.

A further method for introduction of the plasmid into a plant cell is by transformation of plant cell protoplasts (stable or transient). Plant protoplasts are enclosed only by a plasma membrane and will therefore take up macromolecules like exogenous DNA. These engineered protoplasts can be capable of regenerating whole plants. Suitable methods for introducing exogenous DNA into plant cell protoplasts include electroporation and polyethylene glycol (PEG) transformation.

An additional method for introduction of the plasmid into a plant cell is by transformation of plant organelles (such as chloroplast or mitochondria), such as by particle bombardment. Although the plasmid will not replicate in the plant organelles, the exogenous DNA may be incorporated into the genome by recombination.

As used throughout this application, electroporation is a transformation method in which, generally, a high concentration of plasmid DNA (containing exogenous DNA) is added to a suspension of host cell protoplasts, yeast, animal cells, or bacterial cells and the mixture shocked with an electrical field of 200 to 600 V/cm. Following electroporation, transformed cells are identified by growth on appropriate medium containing a selective agent.

As also used throughout this application, particle bombardment (also know as biolistic transformation) of the host cell can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle. Biologically active particles (e.g., dried bacterial cells containing the plasmid and exogenous DNA) can also be propelled into plant cells.

MATERIALS AND METHODS

Plasmids and Viruses

Figure 2:
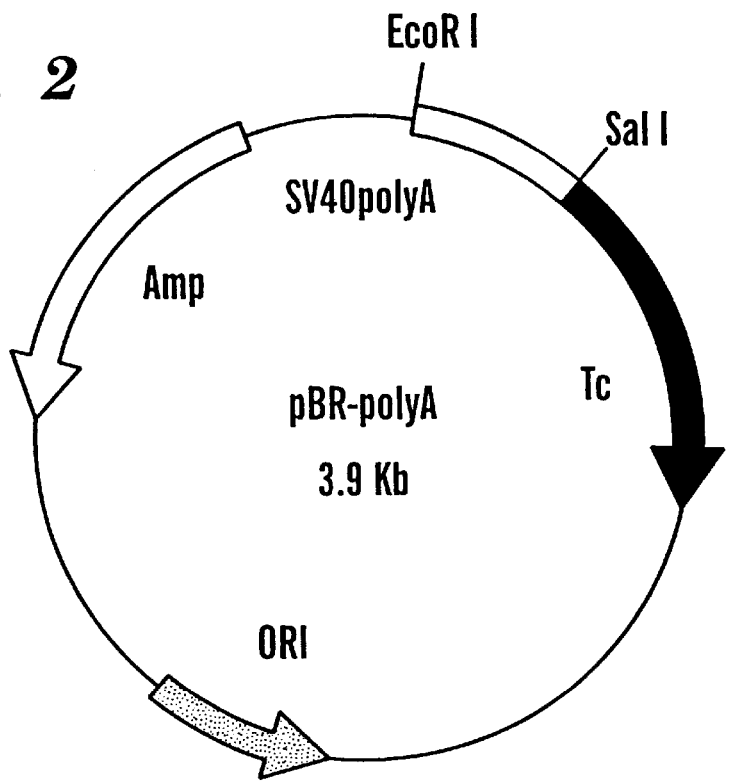
FIG. 2 is a map of the plasmid pBR-polyA.
Figure 5:
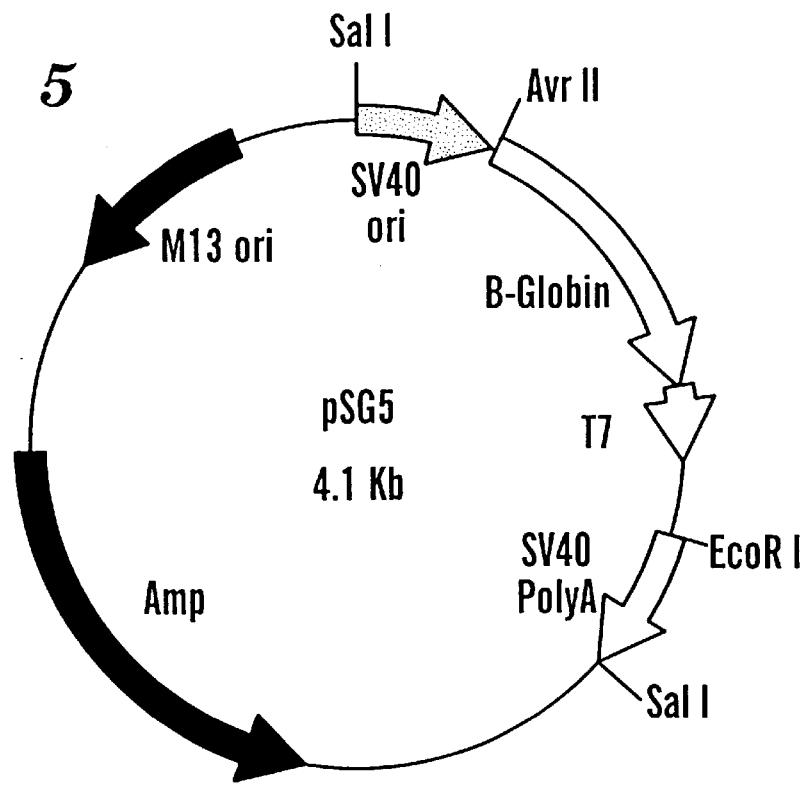
FIG. 5 is a map of the plasmid pSG5.
Figure 6:
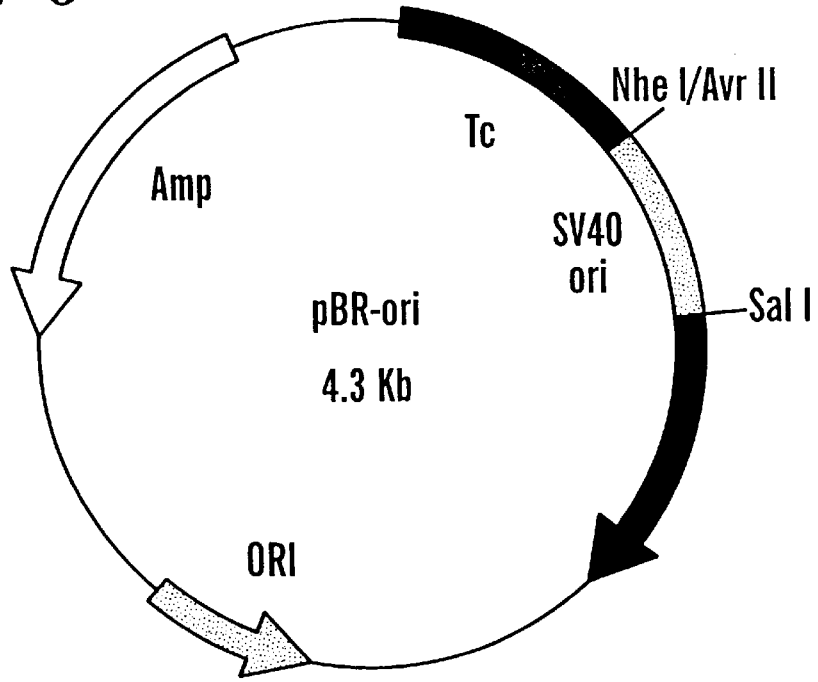
FIG. 6 is a map of the plasmid pBR-ori.
Figure 7:
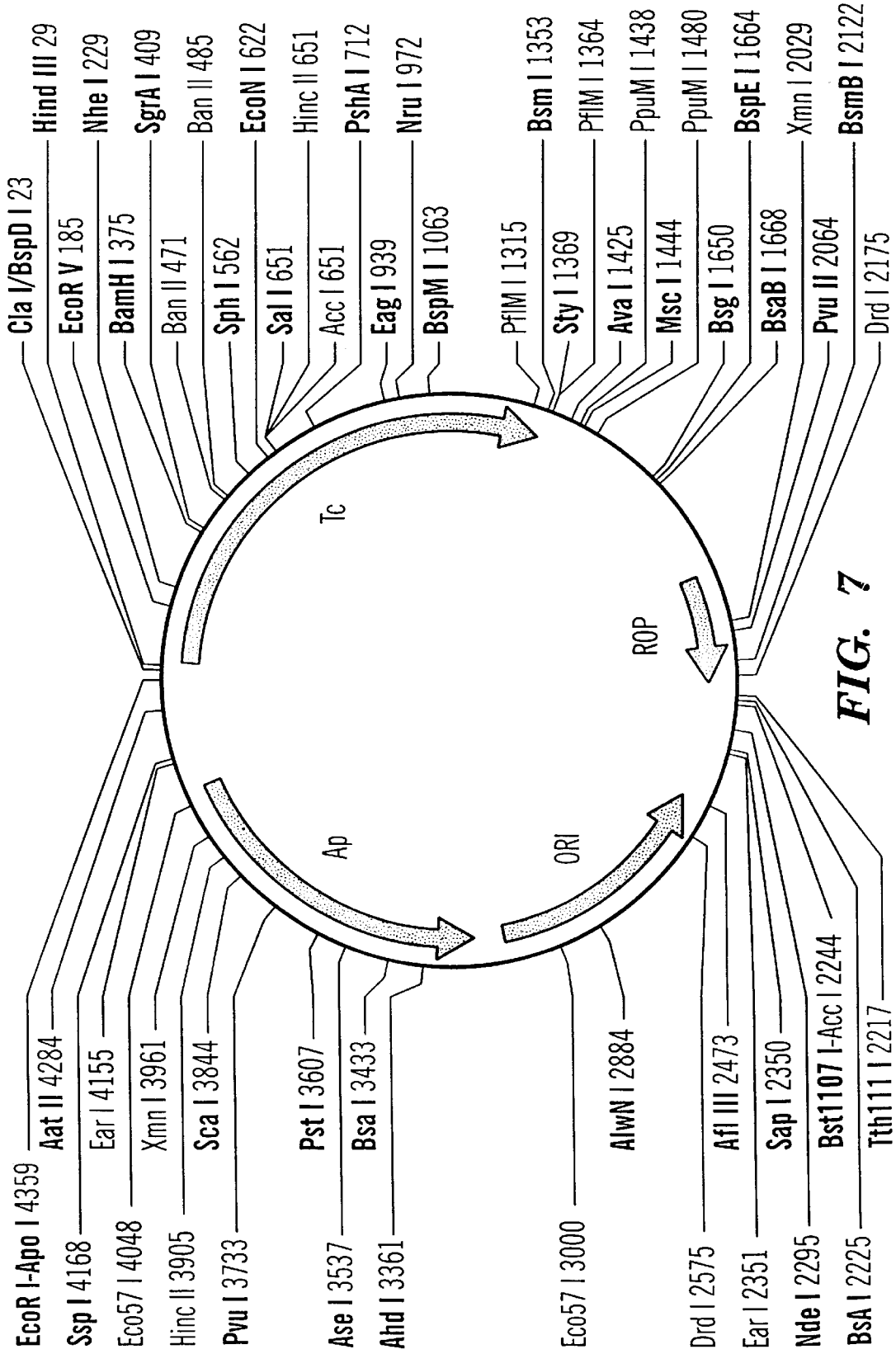
FIG. 7 is a map of the plasmid pBR322 showing the restriction sites for those enzymes which cut the molecule once or twice; the unique sites are shown in bold type.

The plasmid pBR-ori (see FIG. 6), containing the SV40 origin region from SV40 nt 5171 to 294 (SEQ ID NO:1), was constructed by subcloning a 351 bp SalI-AvrII fragment from pSG5 (see FIG. 5) (Stratagene, La Jolla Calif.) in between the SalI and NheI sites of pBR322 (see FIG. 1 and FIG. 7). The plasmid pBR-polyA (see FIG. 2) which contains the SV40 large T antigen polyadenylation signal (nt 2537 to 2668) was constructed by subcloning a 160 bp SalI-EcoRI fragment from pSG5 (see FIG. 5) into the SalI and EcoRI sites of pBR322 (see FIG. 1). The resulting plasmids pBR-ori (see FIG. 6) and pBR-polyA (see FIG. 2) are 4291 bp and 3870 bp, respectively. Plasmid DNA was purified by either alkaline lysis and subsequent CsCl gradient centrifugation or Qiagen midiprep columns. DNA purified in either manner displayed the same intracellular distribution after cytoplasmic microinjection. SV40 DNA was purified from infected TC7 cells as described in Hirt (1967). The plasmid designated pBR322 is commercially available from the American Type Culture Collection (ATCC), 12301 Parklawn Drive, Rockville, Md. 20852, under ATCC Accession numbers 37017 and 31344. SV40 is also available from the ATCC under Accession numbers VR-305 and VR-239. SV40 (strain 776) DNA cloned into plasmid pBR322 is available from the ATCC under Accession numbers 45019 and 45019D. The plasmid designated pSG5 is commercially available from Stratagene (La Jolla, Calif.) under catalogue #216201. The sequence of pBR322 is available through Genbank under accession number J01749. The sequence of SV40 is available through Genbank under accession number J02400.

Cell culture and microinjection

TC7 and Vero cells, sublines of African Green monkey kidney epithelium, Cos-7, NIH3T3, HeLa, and HEp-2 cells were grown on coverslips in DMEM containing 10% fetal bovine serum and cytoplasmically microinjected as described in Dean et al. (1995). CHO cells were grown in McCoy's medium containing 10% fetal bovine serum and similarly microinjected. Primary cultures of human corneal epithelial cells and keratocytes were grown in Opti-MEM medium (Life Technologies, Gaithersburg, Md.) and primary cultures of rat aortic smooth muscle cells were grown in DMEM containing 10% fetal bovine serum. For injection of Tradescantia leaf epidermal cells, leaf peels were made from mature leaves. Purified protein-free DNA was suspended in phosphate-buffered saline and injected at a concentration of 0.5 mg/ml. Assuming that 0.1 pl is delivered by microinjection (Graessmann and Graessmann, 1986), this corresponds to approximately 8,000 molecules of plasmid injected per cell.

For energy depletion studies, the cells were incubated for 8 hours after microinjection in Hank's balanced salts solution containing 6 mM 2-deoxyglucose and 1 µM carbonyl cyanide p-trifluoromethoxyphenylhydrazone (FCCP). For transcription and translation inhibition studies, the cells were pre-incubated for 30 minutes in DMEM containing 10% fetal bovine serum and actinomycin D (10 µg/ml), α-amanitin (5 µg/ml), 5,6-dichloro-1-β-D-ribofuranosylbenzimidazole (DRB; 20 µg/ml), or cyclohexamide (50 µg/ml). The cells were microinjected and subsequently incubated in the presence of the drug for 8 hours at 37° C. The concentrations of co-injected agents were: 0.5 mg/ml WGA and concanavalin A (ConA), and 5 mg/ml mAb414 and IgGκ2a (Sigma, St. Louis Mo). In all cases, the experiments representative of between 50 and 400 visualized cells in at least three independent experiments.

In situ hybridization and indirect immunofluorescence

In situ hybridizations were performed as described in Johnson et al. (1991), but with the following changes. After microinjection and incubation for the appropriate time, the cells were permeabilized with 0.5% Triton X-100 in phosphate-buffered saline at 23° C. for 1 minute, fixed in acetone:methanol (1:1) at −20° C. for 5 minutes, and incubated in 70% formamide in 2×SSC at 70° C. for 2 minutes to denature the DNA. The cells were then hybridized overnight at 37° C. with a fluorescently-labeled probe. All samples were treated with RNaseH (8U/ml) after hybridization and the subsequent washing steps, and the cells were mounted with DAPI and the anti-bleaching reagent DABCO. Fluorescently-labeled probes were prepared by nick translation of pBR322 and SV40 DNA as described in Johnson et al. (1991) except that fluorescein-12-dUTP or Texas Red 5-dUTP (Molecular Probes, Eugene Oreg.) were directly incorporated into the DNA.

After in situ hybridization, anti-SC-35 hybridoma supernatant (a hybridoma cell line producing the anti-SC35 monoclonal antibody is available from the ATCC as Accession number CRL-2031) was reacted with the cells for 2 hours at 37° C. followed by a TRITC-conjugated secondary antibody (Chemicon, Temecula, Calif.).

EXAMPLE I

Nuclear entry of plasmid DNA occurs in the absence of cell division

To characterize the nuclear import of exogenous plasmid DNA by direct means, protein-free SV40 DNA was microinjected into the cytoplasm of TC7 African Green monkey kidney epithelial cells and localized directly by in situ hybridization (Johnson et al., 1991). TC7 cells were cytoplasmically co-injected with rhodamine-BSA, a non-nuclear protein, and approximately 8,000 protein-free DNA molecules and allowed to grow in complete medium for 8 hours. After fixation, in situ hybridizations were performed with fluorescein-dUTP-labeled nick translated SV40 DNA as probe. By 8 hours after injection, the majority of the SV40 DNA was localized in the nucleus. To ensure that the signal represented the injected DNA as opposed to template-derived transcripts, the hybridized samples were treated with RNaseH to degrade any DNA-RNA hybrids (Johnson et al., 1991). Treatment of the injected cells with RNase A to degrade total cellular RNA resulted in the same hybridization staining pattern, confirming that the detected signal is indeed that of the injected DNA. Microscopic observation of the injected cells indicated that the majority had not undergone cell division and the accompanying breakdown of the nuclear envelope. This conclusion was confirmed by the fact that rhodamine-labeled BSA co-injected with the DNA remained in the cytoplasm of the injected cells while the DNA became nuclear. Confocal microscopy was performed on the injected cells to verify that the DNA was accumulating inside the nucleus as opposed to binding to the outside surface of the nuclear envelope. Successive 0.5 µm sections showed that the DNA was indeed inside the nuclei.

Figure 8:
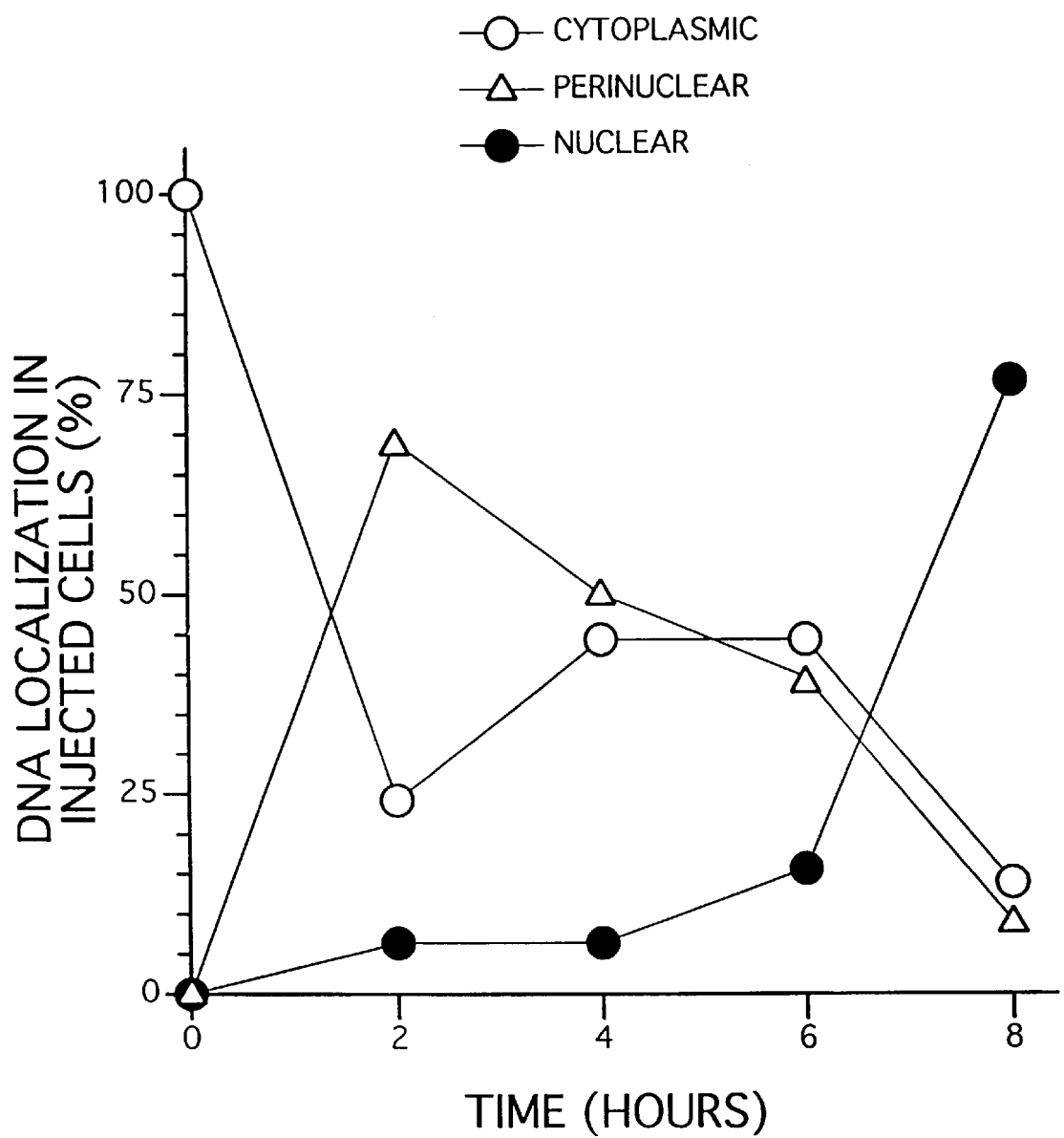
FIG. 8 shows the percentage of cytoplasmic, perinuclear, and nuclear DNA staining obtained using protein-free SV40 DNA microinjected into the cytoplasm of TC7 African Green monkey kidney cells as a function of time.

Time course studies (see FIG. 8) revealed that the DNA was distributed throughout the cytoplasm at early times after injection (less than 4 hours), but by 4 to 6 hours, a distinct perinuclear localization of the DNA signal was seen. By 6 to 8 hours, between 50 and 100% of the cells showed nuclear staining of the DNA, and in the cells that displayed nuclear DNA staining, between 60 and 100% of the fluorescent signal was in the nucleoplasm. In these time course studies, TC7 cells were cytoplasmically-injected with protein-free SV40 DNA, incubated for the indicated times, fixed, and the location of the injected DNA was determined. Cells with cytoplasmic, perinuclear, or nuclear DNA staining were counted and the percent of cells with each staining pattern are shown in FIG. 8. At each time point, between 50 and 100 cells were counted.

This DNA nuclear localization appeared to be a general phenomenon of mammalian cells, rather than due to the permissive nature of the TC7 cells for SV40, since CHO, HeLa, HEp-2, Cos-7, NIH-3T3, Vero cells (another SV40 permissive cell line), human corneal epithelial cells, human keratocytes, and rat aortic smooth muscle cells all displayed similar capacities for DNA nuclear import. In addition, Tradescantia leaf epidermal cells also displayed a similar capacity for DNA nuclear import (see Table 1).

EXAMPLE II

Inhibitors of signal-mediated protein nuclear import also inhibit nuclear localization of plasmid DNA It has been demonstrated that transport of NTS-containing proteins into the nucleus can be inhibited by agents that are thought to occlude the NPC. These include the lectin WGA and antibodies against nucleoporins (Davis and Blobel, 1986; Finlay et al., 1987; Featherstone et al., 1988). When either WGA or the anti-nucleoporin antibody mAb414 was co-injected with SV40 DNA into the cytoplasm of TC7 cells, the DNA remained cytoplasmic at 8 hours post-injection. Co-injection of a control lectin ConA, which does not inhibit NTS-mediated nuclear protein import, or a control isotypic mouse antibody (IgGκ2a) had no effect on the ability of SV40 DNA to localize to the nucleus.

DNA was also excluded from the nucleus when the nucleotide triphosphate pool was depleted in the cells. After injection of DNA, the cells were incubated in Hank's Balanced salts solution containing 2-deoxyglucose and FCCP to inhibit both glycolysis and oxidative phosphorylation. At 8 hours, all of the injected DNA remained in the cytoplasm, whereas in energy-replete cells the DNA was nuclear. These results are all consistent with a model in which the injected DNA enters the nucleus through the NPC.

EXAMPLE III

DNA nuclear import is sequence-specific

In addition to SV40 DNA, the plasmid pBR322 (see FIG. 1) was also injected into the cytoplasm of cells and its subcellular localization was followed over time. Surprisingly, in cells co-injected with both pBR322 (see FIG. 1) and SV40 DNA (see FIG. 4), pBR322 remained completely cytoplasmic while the SV40 DNA migrated to the nucleus as in cells injected with SV40 DNA alone. The plasmid pBR322 also remained cytoplasmic in cells injected with this plasmid alone. This cytoplasmic compartmentalization of pBR322 was constant even at 12 hours post-injection. It has been demonstrated that the rate of nuclear import of non-nuclear proteins and dextrans is inversely proportional to their size (Paine et al., 1975). However, the difference in compartmentalization of the two DNAs was not due to a difference in size since pBR322 is actually 25% smaller than the SV40 genome. To ensure that a pBR322-specific signal could be detected if the DNA was nuclear, pBR322 was injected directly into the nuclei of TC7 cells, and as expected, the staining pattern was nuclear. In addition to pBR322, pBluescript SK+ (Stratagene), which contains additional bacterial and bacteriophage sequences, also remained in the cytoplasm of microinjected cells. The plasmids pSVsmall, pBR-polyA, and pBR-ori were also injected into the cytoplasm of TC7 cells and in situ hybridization were performed 8 hours later. The results are shown in Table 2. These results indicate that plasmid DNA nuclear import is mediated by specific cis-acting sequences.

Figure 3:
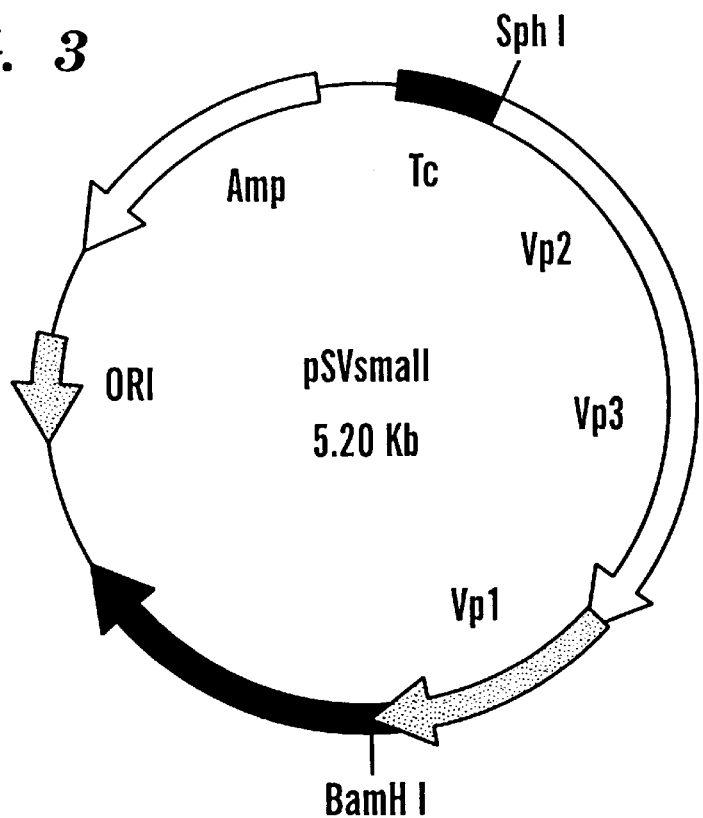
FIG. 3 is a map of the plasmid pSVsmall.

To identify the sequence(s) within the SV40 genome responsible for its nuclear localization, potential regions of the genome were subcloned into pBR322 and tested for their ability to support import into the nucleus. pBR-ori (see FIG. 6), containing the SV40 origin of replication and early promoter, localized to the nucleus to the same extent as did the intact SV40 DNA. In contrast, pBR-polyA (see FIG. 2), containing the T-antigen polyadenylation signal, and pSVs- mall (see FIG. 3), a pBR-SV40 hybrid plasmid lacking the early and late promoters as well as the origin of SV40 (Dean et al., 1995), remained in the cytoplasm. These results indicate that transport of the DNA into the nucleus is sequence-specific and mediated by sequences containing multiple binding sites for eukaryotic transcription and replication factors.

EXAMPLE IV

Localization of plasmid DNA to the nucleus requires transcription

Figure 11:
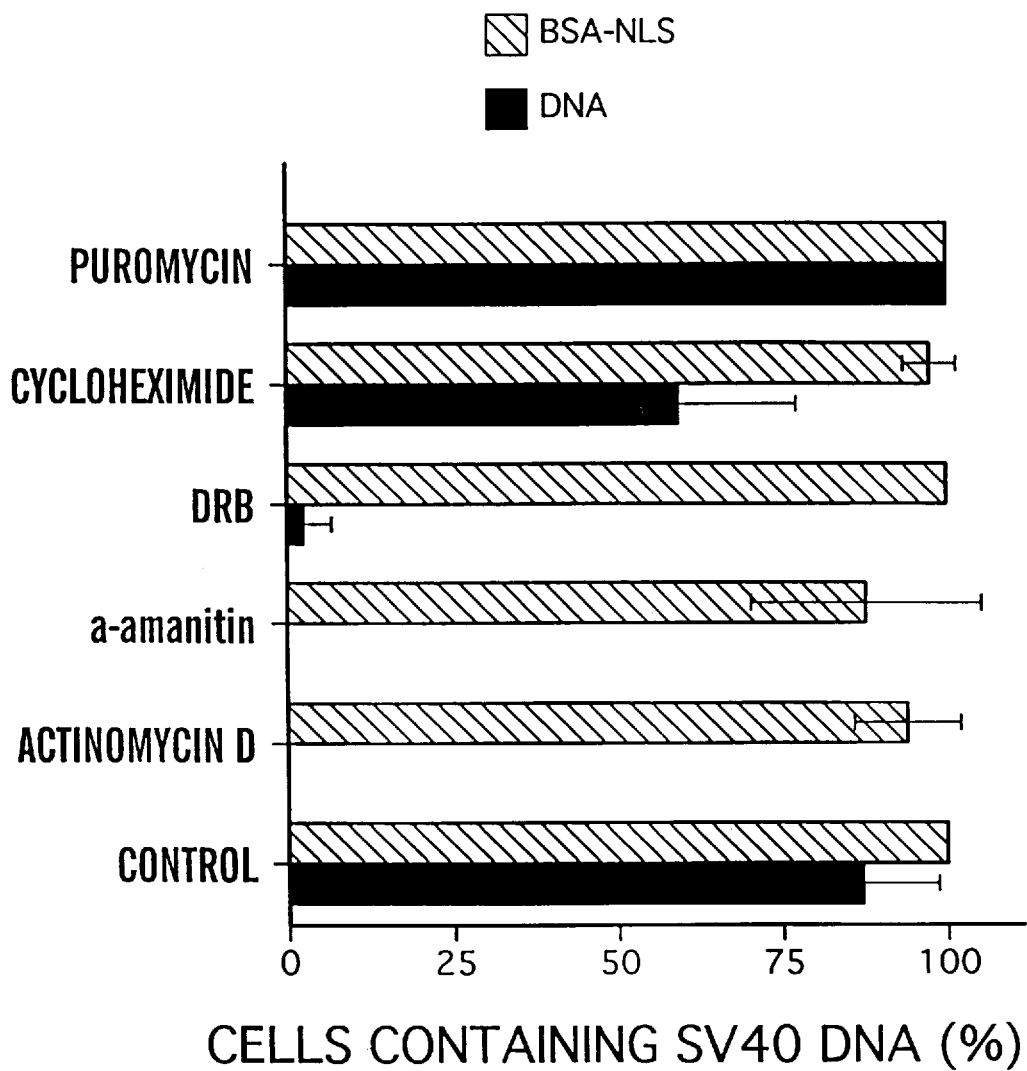
FIG. 11 shows the effect of various agents on the nuclear localization of plasmid DNA and an NTS-containing protein.

There were two patterns of staining of the hybridized SV40 DNA in the nucleus: a diffuse staining throughout the nucleoplasm (but excluding the nucleoli), and a speckled pattern consisting of 10 to 30 foci within the nucleus. Similar staining patterns are obtained when cells are reacted with antibodies against splicing complex proteins (i.e., SC-35). When both the microinjected SV40 DNA and the splicing antigen SC-35 were visualized by in situ hybridization and immunofluorescence, respectively, many of the foci co-localized, suggesting that much of the intranuclear plasmid DNA is localized to areas of active transcription and message processing. When cells cytoplasmically-injected with SV40 DNA were treated independently with agents that act by different mechanisms to inhibit transcription, the DNA remained in the cytoplasm. Treatment of the injected cells with actinomycin D (10 µg/ml), DRB (20 µg/ml), or α-amanitin (5 µg/ml) all showed the same effect (the DNA remained in the cytoplasm). In contrast, inhibition of protein synthesis by treatment of the cells with cyclohexamide (50 µg/ml) had no effect on the ability of SV40 DNA to localize to the nucleus. Incubation of the injected cells with the transcriptional and translational inhibitors did not inhibit all forms of nuclear transport. When a nuclear protein, Rhodamine-BSA-NLS, was injected into the cytoplasm of the cells after 7 hours of incubation in the inhibitors, the protein was still able to partition exclusively to the nucleus as it did in control cells in the absence of any inhibitor. Thus, transcription is required for DNA nuclear import while translation is not (see FIG. 11).

EXAMPLE V

The above results evidence that plasmid DNA can enter the nucleus of a eukaryotic cell in the absence of cell division. This nuclear import of DNA is signal-mediated: while the SV40 DNA genome enters the nucleus, several bacterial plasmids cannot. The sequence of SV40 needed for this import function was mapped to a 372 bp region of DNA that encompasses the SV40 origin of replication, early and late promoters, and the enhancer (nucleotides 5171 to 299 (i.e. SEQ ID NO:1); HindIII to KpnI restriction sites). A method is thus provided for targeting DNA into the nucleic of cells that cannot divide such as terminally differentiated or quiescent cells.

Figure 10:
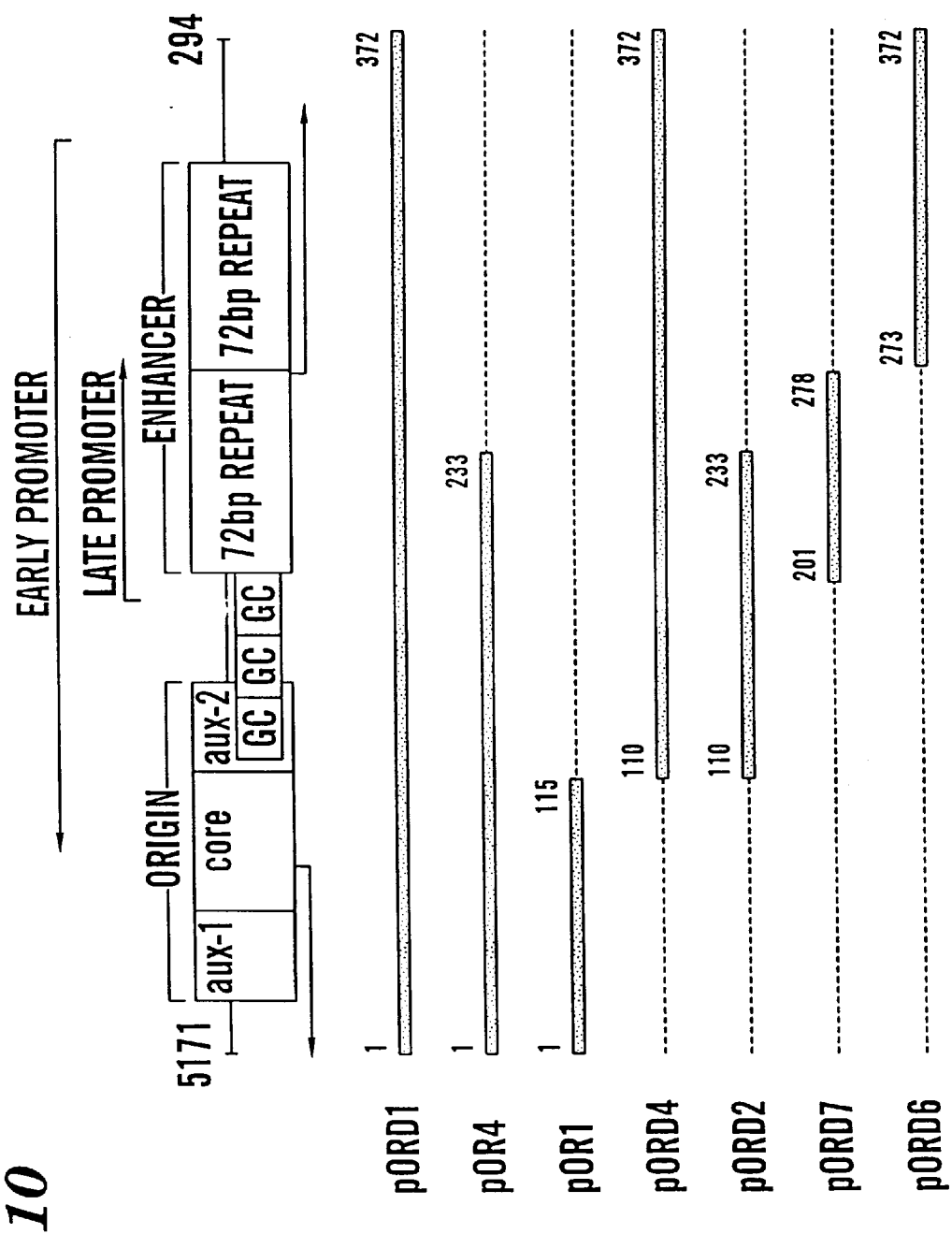
FIG. 10 shows the organization of the SV40 genome from 5171 to 299, and the correspondence of the various plasmids made herein.

Additional plasmid constructs were made that contain various portions of the 372 bp region. FIG. 10 shows these constructs. To identify the SV40 import sequence initially, portions of SV40 were cloned into pBR322, a bacterial plasmid that cannot enter the nucleus, until fragments were found that supported import. The constructs shown in FIG. 10 have been made in both pBR322 and a pBR322 derivative, pOR, that is identical to pBR322 but which lacks pBR322 nucleotides 1092 to 2485 (Luskey & Botchen 1981). This region was shown to interfere with SV40 replication, so all studies of origin structure were subsequently carried out in plasmids lacking this region. Most available origin/promoter mutants have been made in this plasmid. When original mutants were desired, a series of plasmids in pOR (DeLucia et al. 1986; Deb et al. 1987) were used. Consequently, pOR1 was used to construct the other plasmids in FIG. 10 so that the plasmid backbone would be the same in all experiments.

pORD1 contains the 372 bp origin region (5171 to 299=372 (nucleotides 1–372 of SEQ ID NO:1); 372 represents the 366 bp region plus the 6 bp recognition site for KpnI that starts at nucleotide 294 of SEQ ID NO:1; thus the 272 fragment goes from 5171 to 299 in the SV40 genome). This plasmid is functionally identical to pERori as discussed above, except that is is made in pOR1 from SV40 DNA, not in pBR322 from the Stratagene plasmid pSG5 (which contains the SV40 origin). pORD1 is imported into the nucleus in 62% of cells; intact SV40 is imported in 81% of the cells. In Table 3, the 62% is set to 100% and the other constructs are compared to the 372 bp region.

pOR1 is imported in 7% of the cells. Thus, the important sequence is not in this fragment, but, 7% (in 6 experiments and about 500 cells) is statistically different from 0% seen for pBR322. This means that this sequence does contain a portion that can promote import, albeit not very well.

pOR4 is imported at 55% that of the 372 bp plasmid. pORD2 contains only the DNA in pOR4 that is not in pOR1 (37 to 160 of SV40; nucleotides 110–233 of SEQ ID NO:1). This plasmid is imported 90% relative to the total 372. Thus, the region from 5171 to 37 of SV40 (nucleotides 1–115 of SEQ ID NO:1) contains an element that has a slight negative effect on the region from 37 to 160 of SV40 (nucleotides 110–233 of SEQ ID NO:1).

Most of the import activity remains in nucleotides 37 to 294 of SV40 (nucleotides 110–372 of SEQ ID NO:1) (pORD4). pORD2 and pORD6 are not overlapping but each support import to the same level. pORD7 is only 77 bp in length (nucleotides 201–278 of SEQ ID NO:1), but also has almost full activity.

Thus, multiple sequences within the 372 bp fragment can support nuclear import. The common element to pORD2, 4, 6, and 7 is the presence of the SV40 enhancer. Referring to FIG. 10, there are two repeats of the enhancer, one in pORD2 and 4, and the other in pORD2 and 6. pORD7 straddles the end of one repeat and the beginning of the other.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

| CELLS | NUCLEAR IMPORT OF SV40 DNA |
|---|---|
| TC7 | + |
| Vero | + |
| HeLa | + |
| CHO | + |
| Cos-7 | + |
| NIH 3T3 | + |
| Human corneal epithelial cells | + |
| Hutnan Keratocytes | + |
| Rat aortic smooth muscle cells | + |
| Tradescantia leaf epidermal cells | + |

TABLE 2

| DNA | Nuclear Localization (% injected cells ± sd) |
|---|---|
| SV40 | 81 ± 12 |
| pBR322 | 0 ± 1 |
| pBluescript SK | 0 ± 0 |
| pSVsmall | 0 ± 0 |
| pBR-polyA | 2 ± 1 |
| pBR-ori | 62 ± 17 |

TABLE 3

| Plasmid | Size in bp | Nucleotides of SEQ ID NO:1 (and SV40) | Nuclear Import (% Cells) | Import Ability (%) Relative to 366 bp Sequence |
|---|---|---|---|---|
| pORD1 | 372 | 1–372 (5171 to 299) | 62 | 100 |
| pOR4 | 233 | 1–233 (5171 to 160) | 34 | 55 |
| pOR1 | 115 | 1–115 (5171 to 37) | 7 | 11 |
| pORD4 | 262 | 110–372 (37 to 299) | 58 | 94 |
| pORD2 | 123 | 110–233 (37 to 160) | 56 | 90 |
| pORD7 | 77 | 201–278 (128 to 205) | 55 | 89 |
| pORD6 | 99 | 273–372 (200 to 299) | 57 | 92 |
| pBR322 | | | 0 | 0 |
| (entire SV40 genome) | | | 81 | 130 |

REFERENCES

Adam, E. J. H. and S. A. Adam, *J Cell Biol* 125:547–555 (1994).
Allen, R. E., et al., *J Cell Physiol* 165:307–312 (1995).
Baru, M., et al., *Gene* 161(2):143–150 (1995).
Berns, K. I. and C. Giraud, *Ann N.Y. Acad Sci* 772:95–104 (1995).
Betz, A. L., et al., *J Cereb Blood Flow Metab* 15(4):547–551 (1995).
Brownlee, G. G., *Br Med Bull* 51(1):91–105 (1995).
Bukrinsky, M. I., et al., Nature 365:666–669 (1993).
Bukrinsky, M. I., et al., *Proc Natl Acad Sci USA* 89:6580–6584 (1992).
Cserpan, I. and A. Udvardy, *J Cell Sci* 108:1849–1861 (1995).
Cotran, R. S., et al., *Robbins Pathologic basis of Disease*, 5th ed., W. B. Saunders Co., Philadelphia, Pa., pp 36–37 (1994).
Datta, S., *Development* 121:1173–1182 (1995).
Davis, L. I. and G. Blobel, *Cell* 45:699–709 (1986).
Dean, D. A. and H. Kasamatsu, *J Biol Chem* 269:4910–4916 (1994).
Dean, D. A., et al., *J Virol* 69:1115–1121 (1995).
Deb et al., *J Virol* 61:2143 (1987).
DeLucia et al., *J Virol* 57:138 (1986).
Dowty, M. E., et al., *Proc Natl Acad Sci USA* 92:4572–4576 (1995).
Ekhterae, D. and J. C. Stanley, *J Vasc Surg* 21(6):953–962 (1995).
Escudero, J., et al., *Proc Natl Acad Sci USA* 92:230–234 (1995).

Featherstone, C., et al., *J Cell Biol* 107:1289–1297 (1988).
Fields, B. N., et al., Eds., *Virology*, Raven Press, New York (1990).
Fiers, W., et al., *Nature* 273:113–119 (1978).
Finlay, D. R., et al., *J Cell Diol* 104:189–200 (1987).
Görlich, D., et al., *Cell* 79:767–778 (1994).
Graessmann, M. and A. Graessmann, in *Microinjection and Organelle Transplantation Techniques*, J. E. Celis, et al., eds, Academic Press, London, pp. 3–37 (1986).
Hamm, J., et al., *Cell* 62:569–577 (1990).
Hicks, G. R. and N. V. Raikhel, *Annu Rev Cell Dev Biol* 11:155–188 (1995).
Hirt, B., *J Mol Biol* 26:365–369 (1967).
Johnson, C. V., et al., *Meth Cell Biol* 35:73–99 (1991).
Knowles, M. R., et al., *N Engl J Med* 333(13):823–831 (1995).
Kojima, H., et al., *Biochem Biophys Res Commun* 212(2):712–717 (1995).
Langan, T. J. and M. C. Slater, *Brain Res* 548:9–17 (1991).
Licht, I., et al., *Blood* 86:111–121 (1995).
Luskey and Botchen, *Nature* 293:79 (1981).
Melchoir, F. and L. Gerace, *Curr Opinion Cell Biol* 7:310–318 (1995).
Melchoir, F., et al., *J Cell Biol* 123:1649–1659 (1993).
Michaud, N. and D. Goldfarb, *J Cell Biol* 116:851–861 (1992).
Michaud, N. and D. S. Goldfarb, *J Cell Biol* 112:215–223 (1991).
Miller, L. K., *Bioessays* 11:91–95 (1989).
Moore, M. S. and G. Blobel, *Nature* 365:661–663 (1993).
Moore, M. S. and G. Blobel, *Proc Natl Acad Sci USA* 91:10212–10216 (1994).
Moroianu, J., et al., *Proc Natl Acad Sci USA* 92:2008–2011 (1995).
Newmeyer, D. D. and D. J. Forbes, *Cell* 52:641–653 (1988).
O'Neill, R. E., et al., *Proc Natl Acad Sci USA* 270:22701–22704 (1995).
Osborne, W. R., et al., *Proc Natl Acad Sci USA* 92(17):8055–8058 (1995).
Paine, P. L., et al., *Nature* 254:109–114 (1975).
Phaneuf, D., et al., *Biochem Biophys Res Comm* 208(3):957–963 (1995).
Ponchio, L., et al., *Blood* 86:3314–3321 (1995).
Porth, C. M., *Pathophysiology: Concepts of altered health states*, 4th ed., J. B. Lippincott Co., Philadelphia, Pa., pp 72–74 (1994).
Radu, A., et al., *Proc Natl Acad Sci USA* 92:1769–1773 (1995).
Reddy, V. B., et al., *Science* 200:494–502 (1978).
Richardson, W. D., et al., *Cell* 52:655–664 (1988).
Rowland, R. T., et al., *Ann Thorac Surg* 60(3):721–728 (1995).
Sambrook et al., *Molecular Cloning: A Laboratory Manual*, 2d Edition, Cold Spring Harbor Laboratory Press, Cold Spring Harbor, N.Y. (1989).
Scanlon, K. J., et al., *FASEB J* 9:1288–1296 (1995).
Seshadri, T. and J. Campisi, *Exp Gerontol* 24:515–522 (1989).
Shimizu, R. T., et al., *J Biol Chem* 270:7631–7643 (1995).
Stamatoyannopoulos, J. A. and A. W. Nienhuis, in *The Molecular Basis of Blood Diseases*, 2d Edition, Stamatoyannopoulos et al., eds., W. B. Saunders Co., Philadelphia Pa., pp. 107–156 (1994).
Stevenson, S. C., et al., *Arterioscler Thromb Vasc Biol* 15(4):479–484 (1995).
Sullenger, B. A. and T. R. Cech, *Nature* 371:619–622 (1994).
Vallejos, et al., *Genetics* 112:93–105 (1986).
Vaulont, S., et al., *Transgenic Res* 4(4):247–255 (1995).
Vick, R. S., et al., *J Neurosci Res* 33:75–81 (1992).
Vrionis, F. D., et al., *J Neurosurg* 83(4):698–704 (1995).
von Schwedler, U., et al., *Proc Natl Acad Sci USA* 91:6992–6996 (1994).
Weis, K., et al., *Science* 268:1049–1053 (1995).
Young, J. C., et al., *Blood* 87:545–556 (1996).
Zupan, J. R. and P. Zambryski, *Plant Physiol* 107:1041–1047 (1995).

---

What is claimed is:

1. A nuclear targeting molecule having a nucleic acid sequence which consists of SEQ ID NO:1 or a nuclear targeting portion of SEQ ID NO:1, wherein the nuclear targeting portion of SEQ ID NO:1 is selected from the group consisting of nucleotides 1 to 233 of SEQ ID NO:1, 1 to 115 of SEQ ID NO:1, 110 to 372 of SEQ ID NO:1, 110 to 233 of SEQ ID NO:1, 201 to 278 of SEQ ID NO:1, and 273 to 372 of SEQ ID NO:1.

2. A plasmid comprising:
  a nuclear targeting molecule having a nucleic acid sequence which consists of SEQ ID NO:1 or a nuclear targeting portion of SEQ ID NO:1, wherein the nuclear targeting portion of SEQ ID NO:1 is selected from the group consisting of nucleotides 1 to 233 of SEQ ID NO:1, 1 to 115 of SEQ ID NO:1, 110 to 372 of SEQ ID NO:1, 110 to 233 of SEQ ID NO:1, 201 to 278 of SEQ ID NO:1, and 273 to 372 of SEQ ID NO:1; and
  a DNA molecule to be targeted to a nucleus of a host cell.

3. The plasmid of claim 2 wherein the plasmid further comprises a molecule encoding a selection marker.

4. The plasmid of claim 2 wherein the plasmid further comprises a bacterial origin of replication.

5. The plasmid of claim 2 wherein the plasmid further comprises a molecule encoding a promoter, expression of said DNA molecule to be targeted to a nucleus being under control of said promoter.

6. The plasmid of claim 2 wherein the plasmid further comprises a molecule to direct integration of the DNA molecule into the genome of a host cell.

7. The plasmid of claim 2 wherein the plasmid further comprises unique restriction sites for insertion of additional molecules.

8. A host cell comprising the plasmid of claim 2.

9. A viral vector comprising the plasmid of claim 2.

10. The plasmid of claim 3 wherein said selection marker is an antibiotic resistance marker.

11. The plasmid of claim 6 wherein the molecule to direct integration is a viral integration sequence.

12. The plasmid of claim 7 wherein said unique restriction sites are provided by a polylinker.

13. The host cell of claim 8 wherein the host cell is a bacterial cell.

14. The host cell of claim 8 wherein the host cell is a mammalian cell.

15. The host cell of claim 8 wherein the host cell is a plant cell.

16. The host cell of claim 8 wherein the host cell is a yeast cell.

17. The host cell of claim 8 wherein the host cell is an insect cell.

18. The host cell of claim 8 wherein the host cell is a non-dividing cell.

19. The host cell of claim 18 wherein the non-dividing cell is a quiescent cell.

20. The host cell of claim 18 wherein the non-dividing cell is a terminally differentiated cell.

21. The viral vector of claim 9 wherein the viral vector is selected from the group consisting of an adenovirus vector, a retrovirus vector, an adenovirus-associated virus vector, a vaccinia vector, and a herpes simplex virus vector.

22. A host cell into which the viral vector of claim 9 has been introduced.

23. The host cell of claim 22 wherein the host cell is a mammalian cell.

24. The host cell of claim 22 wherein the host cell is a plant cell.

25. The host cell of claim 22 wherein the host cell is a yeast cell.

26. The host cell of claim 22 wherein the host cell is an insect cell.

27. The host cell of claim 22 wherein,the host cell is a non-dividing cell.

28. The host cell of claim 27 wherein the non-dividing cell is a quiescent cell.

29. The host cell of claim 27 wherein the non-dividing cell is a terminally differentiated cell.

30. A method of targeting a DNA molecule into a nucleus of a host cell, said method comprising:
  providing a plasmid for targeting a DNA molecule into a nucleus of a host cell, the plasmid comprising a nuclear targeting molecule having a nucleic acid sequence which consists of SEQ ID NO:1 or a nuclear targeting portion of SEQ ID NO:1, wherein the nuclear targeting portion of SEQ ID NO:1 is selected from the group consisting of nucleotides 1 to 233 of SEQ ID NO:1, 1 to 115 of SEQ ID NO:1, 110 to 372 of SEQ ID NO:1, 110 to 233 of SEQ ID NO:1, 201 to 278 of SEQ ID NO:1, and 273 to 372 of SEQ ID NO:1, and the plasmid further comprising a DNA molecule to be targeted to a nucleus of a host cell; and
  introducing said plasmid into the cytoplasm of said host cell, wherein said nuclear targeting molecule targets said DNA molecule into the nucleus of said host cell.

31. The method of claim 30 wherein said host cell is a non-dividing cell.

32. The method of claim 30 wherein said plasmid is introduced into the cytoplasm of the host cell by a method selected from the group consisting of: microinjection, electroporation, calcium phosphate coprecipitation, DEAE dextran introduction, liposome mediated introduction, viral mediated introduction, naked DNA injection, and biolistic bombardment.

* * * * *